(12) United States Patent
Coligado

(10) Patent No.: US 6,656,144 B1
(45) Date of Patent: Dec. 2, 2003

(54) ARTICULATING JOINT FOR AN ORTHOPEDIC BRACE

(75) Inventor: Joseph Coligado, Melrose Park, IL (US)

(73) Assignee: Hipbolt Orthopedic Systems, Melrose Park, IL (US)

(*) Notice: Subject to any disclaimer, the term of this patent is extended or adjusted under 35 U.S.C. 154(b) by 345 days.

(21) Appl. No.: 09/721,418

(22) Filed: Nov. 22, 2000

Related U.S. Application Data

(60) Provisional application No. 60/166,921, filed on Nov. 22, 1999, and provisional application No. 60/195,803, filed on Apr. 10, 2000.

(51) Int. Cl.⁷ .............................. A61F 2/64; A61F 5/00
(52) U.S. Cl. .............................. 602/16; 602/23; 602/26
(58) Field of Search .............................. 602/16, 23, 26, 602/5; 623/39

(56) References Cited

U.S. PATENT DOCUMENTS

| | | | |
|---|---|---|---|
| 4,337,764 A | | 7/1982 | Lerman |
| 4,620,532 A | * | 11/1986 | Houswerth .................. 602/26 |
| 5,000,169 A | * | 3/1991 | Swicegood .................. 602/26 |
| 5,399,149 A | * | 3/1995 | Frankowiak .................. 602/16 |
| 5,421,810 A | | 6/1995 | Davis et al. |
| 5,437,619 A | * | 8/1995 | Malewicz et al. .................. 602/20 |
| 5,460,599 A | * | 10/1995 | Davis .................. 602/26 |
| 5,885,235 A | * | 3/1999 | Opahle .................. 602/16 |
| 5,954,677 A | * | 9/1999 | Albrecht .................. 602/16 |
| 6,090,057 A | * | 7/2000 | Collins .................. 602/16 |
| 6,203,511 B1 | * | 3/2001 | Johnson et al. .................. 602/16 |
| 6,375,632 B1 | * | 4/2002 | Albrecht .................. 602/16 |

FOREIGN PATENT DOCUMENTS

| | | | | |
|---|---|---|---|---|
| DE | 19933197 A1 | * | 2/2001 | .................. 602/16 |
| EP | 0841044 A1 | * | 5/1998 | .................. 602/16 |

* cited by examiner

*Primary Examiner*—Nicholas D. Lucchesi
*Assistant Examiner*—Victor K. Hwang
(74) *Attorney, Agent, or Firm*—Pauley Petersen & Erickson

(57) ABSTRACT

An articulating joint for an orthopedic brace wherein a moveable plate is rotatably connected with respect to a fixed plate. The moveable plate includes a plurality of adjustment apertures positioned around a first axis of rotation wherein one or more coarse limit screws are positioned within the adjustment apertures to limit the range of motion between the moveable plate and the fixed plate within a predetermined arc of rotation. Fine adjustment means are preferably positioned with respect to the fixed plate and obstruct a range of motion of the coarse limit screws. In addition, interchangeable struts are attached to the moveable plate and/or the fixed plate to facilitate connection to the orthopedic brace and custom sizing wherein at least one of the struts is moveable around a second axis of rotation.

21 Claims, 6 Drawing Sheets

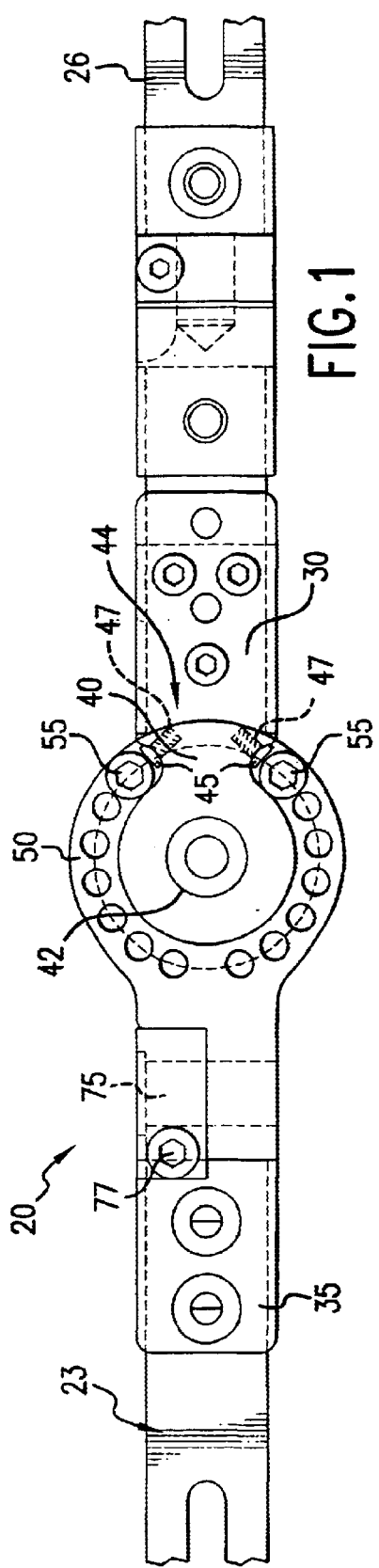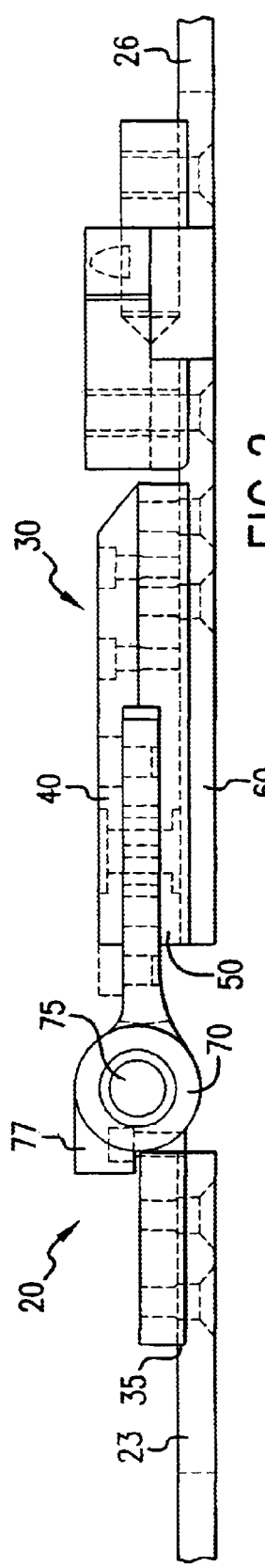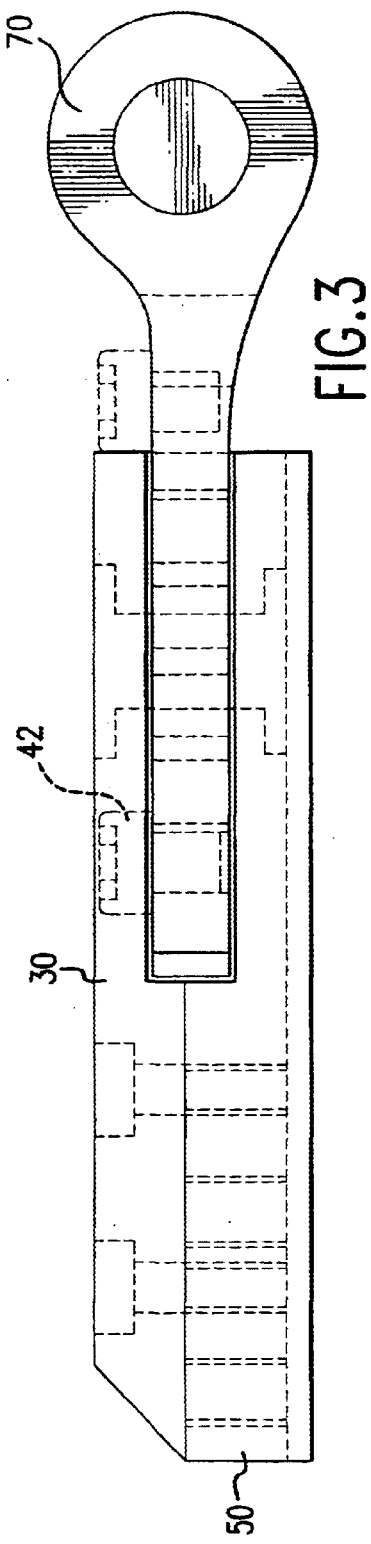

ARTICULATING JOINT FOR AN ORTHOPEDIC BRACE

CROSS REFERENCE TO RELATED APPLICATIONS

This application claims the benefit of U.S. Provisional Application Nos. 60/166,921, filed Nov. 22, 1999 and 60/195,803, filed Apr. 10, 2000.

BACKGROUND OF THE INVENTION

1. Field of the Invention

This invention relates to an articulating joint for an orthopedic brace for use in post-operative rehabilitation and/or to combat the effects of chronic disease. More specifically, this invention relates to an articulating joint that permits adjustment of a fixed arc of rotation for orthopedic braces to provide dependable and predictable movement for a patient.

2. Description of Related Art

Conventional orthopedic braces, such as pelvic braces and knee braces, generally require an articulating joint to connect a first brace or cuff on one side of the affected joint with a second brace or cuff on the other side of the affected joint. For example, many conventional pelvic braces include a hip brace connected to a thigh cuff. The joint between the hip brace and the thigh cuff traditionally requires a limit to the range of motion or rotation that the patient may exert on the affected joint. As such, an articulating joint should be adjustable between a first point and a second point along an arc of rotation. More preferably, an articulating joint should be adjustable to permit and/or prevent abduction, adduction, flexion, extension and rotation.

Further, conventional articulating joints are generally compatible with only one type or brand of orthopedic brace. Thus, conventional articulating joints are not compatible with many of the existing orthopedic braces.

SUMMARY OF THE INVENTION

Conventional orthopedic braces, such as hip braces typically include two parts, such as a thigh cuff and a hip brace, which are connected with an articulating joint. The articulating joint, referred to as a joint herein, limits the range of motion of the patient's hip, knee, elbow or other joint by limiting the permissible range of motion between the two parts, such as between the hip brace and the thigh cuff. Preferably, the joint limits the range of motion in all planes, including abduction, adduction, flexion, extension and rotation.

According to one preferred embodiment of this invention, a joint is positioned between two struts for limiting the rotational motion between the two struts. One strut is preferably attached with respect to the hip brace and the other strut is preferably attached with respect to the thigh cuff.

The joint preferably comprises a fixed plate and a moveable plate. The fixed plate may comprise a top plate and a bottom plate which together formed the fixed plate through which the moveable plate rotates.

The fixed plate (the top plate and the bottom plate) are preferably sandwiched around the moveable plate which preferably rotates freely between the top plate and the bottom plate. The moveable plate is preferably attached with respect to a first strut and the fixed plate is preferably attached with respect to a second strut opposite the first strut.

The rotation of the moveable plate between the top plate and the bottom plate is preferably adjustable within a range of motion between slightly greater than 0° and less than 360°. The joint is preferably adjustable to permit incremental adjustments of 5° or less across the possible range of motion. Therefore, the joint is adjustable to permit a range of motion for a patient between virtually any two desirable angles of rotation.

The fixed plate preferably comprises a generally circular center section having threaded bores positioned at either end of an axis pin. Fine limit screws are preferably positioned within one or both of the threaded bores depending upon the desired setting of the joint. The fine limit screws may include washers or vary in length to accommodate a range of adjustments. The fine limit screws may be color coded to permit simple reference to a desired adjustment. Therefore, one color screw may correspond to a 5° adjustment and another color screw may correspond with a 2.5° adjustment.

The moveable plate is preferably generally round and includes a plurality of threaded bores spaced around a periphery of the moveable plate. Coarse limit screws may be inserted into the desired threaded bores within the moveable plate to create outer limits of rotation for the moveable plate between the top plate and the bottom plate. Accordingly, when a coarse limit screw is placed in each of two threaded bores in the moveable plate, the moveable plate rotates until the coarse limit screw contacts either the fine adjustment screw or a center portion of the fixed plate.

According to one preferred embodiment of this invention, threaded bores in the moveable plate are positioned at equal intervals around the periphery of the moveable plate. Therefore, coarse limit screws permit rotational adjustment in equal increments, such as 20°, and fine adjustment screws in the fixed plate permit rotational adjustment in smaller increments, such as 5°.

It is one object of this invention to provide an articulating joint which provides sufficient adjustability along at least one arc of rotation to limit the movement of the orthopedic brace thereby controlling the range of motion in at least one and preferably all planes of the patient's affected joint.

It is another object of this invention to provide an articulating joint which permits fine adjustment of the arc of rotation between a moveable plate and a fixed plate.

It is yet another object of this invention to provide an articulating joint that permits rotation between a first strut and the articulating joint around a second axis of rotation for further adjustment.

It is still another object of this invention to provide an articulating joint that permits the connection of interchangeable struts to accommodate custom sizing and multiple orthopedic brace styles and manufacturers.

It is yet another object of this invention to provide an articulating joint that maintains a fixed arc of rotation within a first axis of rotation and maintains a fixed position within a second axis of rotation.

BRIEF DESCRIPTION OF THE DRAWINGS

The above-mentioned and other features and objects of this invention will be better understood from the following detailed description taken in conjunction with the drawings wherein:

FIG. 1 is front view of a joint according to a preferred embodiment of this invention;

FIG. 2 is a side view of the joint shown in FIG. 1;

FIG. 3 is a close-up side view of the fixed plate and the moveable plate according to a preferred embodiment of this invention;

DESCRIPTION OF PREFERRED EMBODIMENTS

Figure 4:
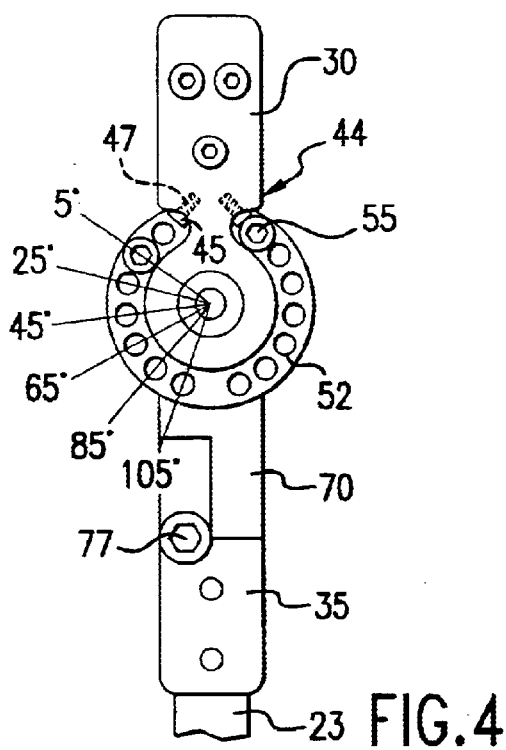
FIG. 4 is a front view of a joint showing angles of adjustment according to one preferred embodiment of this invention.

According to one preferred embodiment of this invention, joint 20 is positioned between two struts 23, 26 for limiting the rotational motion between the two struts 23, 26. First strut 23 is preferably attached with respect to one half of an orthopedic brace, such as hip brace 15 and second strut 26 is preferably attached with respect to thigh cuff 18.

As used in the Specification and Claims, the term rotation refers to movement between two specific components and does not generally refer to a medical term of art. The joint according to this invention is designed to permit and/or limit the range of motion of a patient in one or more, and preferably all, planes of movement. Such planes of movement include abduction, adduction, flexion, extension and rotation.

As shown in FIGS. 1–6, joint 20 preferably comprises fixed plate 30 and moveable plate 50. Fixed plate 30 and moveable plate 50 are preferably machined from steel, such as 1045 steel, for rigidity and durability. Due to the stresses involved in orthopedic braces and the importance of maintaining desired settings of such braces, all material and components described herein are preferably fabricated from rigid and durable materials.

According to a preferred embodiment of this invention, fixed plate 30 comprises top plate 40 and bottom plate 60. Top plate 40 may be a separately attachable component from bottom plate 60 or alternatively may comprise an integrated, unitary fixed plate 30 having top plate 40 and bottom plate 60 as distinct portions of the unitary whole. As used in the specification and claims, fixed plate 30 may comprise top plate 40 and bottom plate 60 as described herein or may otherwise comprise any other suitable unitary or multi-piece component.

Fixed plate 30 is preferably positioned around moveable plate 50 which preferably rotates freely within fixed plate 30, such as between top plate 40 and bottom plate 60. Axis pin 42 preferably connects moveable plate 50 with respect to fixed plate 30 whereby axis pin 42 follows an axis of rotation of moveable plate 50, herein referred to as a first axis of rotation. As described in more detail below, moveable plate 50 is preferably attached with respect to first strut 23 and fixed plate 30 is preferably attached with respect to second strut 26, opposite first strut 23.

Top plate 40 portion of fixed plate 30 preferably comprises a generally circular center section having fine adjustment means 44, such as threaded bore 47, positioned at either end of axis pin 42 as shown in the figures. Fine limit screws 45 are preferably positioned within one or both of threaded bores 47, depending upon the desired setting of the joint.

Bottom plate 60 is positioned on an opposite side of moveable plate 50 as top plate 40. Preferably bottom plate 60 and top plate 40 are connected through a center connection or hub, such as axis pin 42, that permits rotation of moveable plate 50 between bottom plate 60 and top plate 40. Top plate 40 and bottom plate 60 may be reversed and still effect the desired mechanism.

The rotation of moveable plate 50 between top plate 40 and bottom plate 60 is preferably adjustable within a range of motion between slightly greater than 0° and less than 360°. As described below, joint 20 is preferably adjustable to permit incremental adjustments of 5° or less across the possible range of motion. Therefore joint 20 is adjustable to permit a range of motion for a patient between virtually any two desirable angles of rotation.

Moveable plate 50 is preferably generally round and includes a plurality of adjustment apertures 52 spaced around moveable plate 50, more specifically around a first axis of rotation of moveable plate 50. According to one preferred embodiment of this invention, adjustment apertures 52 are equally spaced around a periphery of moveable plate 50, preferably at equal radial increments. Adjustment apertures 52 may be threaded or configured in any manner to permit attachment of coarse limit screws 55.

Figure 5:
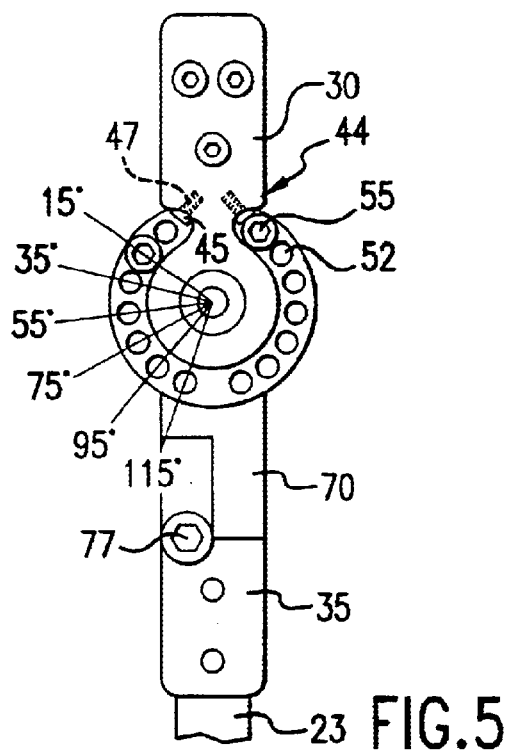
FIG. 5 is a front view of a joint showing angles of adjustment according to one preferred embodiment of this invention.
Figure 6:
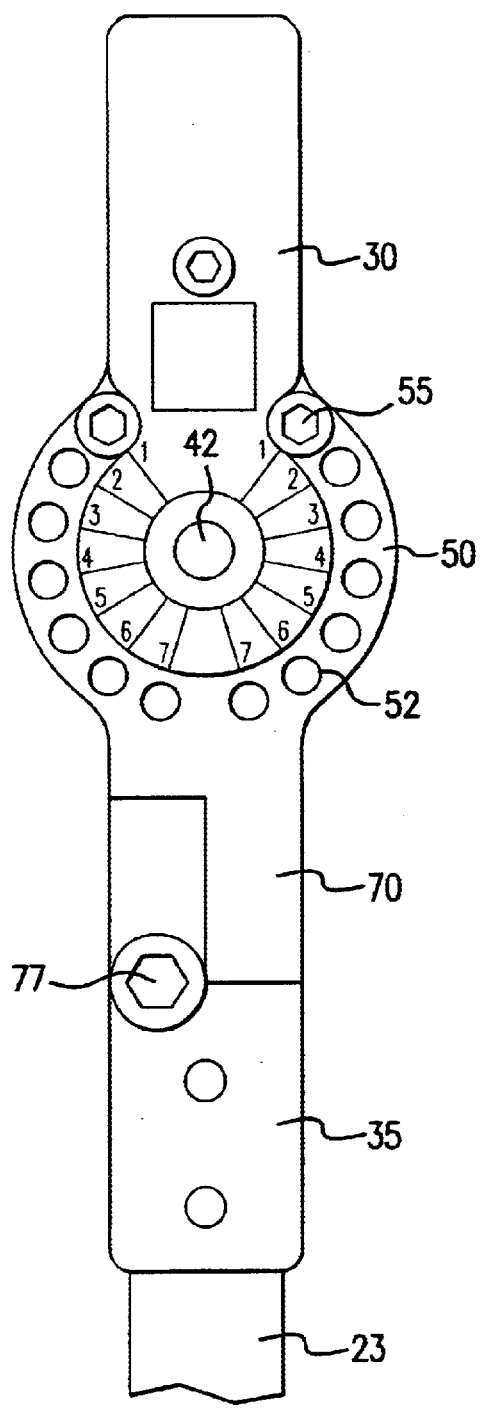
FIG. 6 is a front view of a joint according to one preferred embodiment of this invention.

As shown in FIGS. 4–6, coarse limit screws 55 may be inserted into the desired adjustment apertures 52 within moveable plate 50 to create outer limits of rotation for moveable plate 50 within fixed plate 30, specifically between top plate 40 and bottom plate 60. Coarse limit screws 55 are preferably threaded set screws although alternative embodiments may be possible without threads provided coarse limit screws maintain a set position within the desired adjustment aperture 52. Accordingly, when coarse limit screw 55 is placed in each of typically two adjustment apertures 52 in moveable plate 50, moveable plate 50 rotates until limit screw 55 contacts either fine adjustment screw 45 or portion of top plate 40 around threaded bores 47.

According to one preferred embodiment of this invention shown in FIGS. 4–6, adjustment apertures 52 in moveable plate 50 are positioned at 20° intervals around the periphery of moveable plate 50. Therefore, coarse limit screws 55 permit rotational adjustment in 20° increments and fine adjustment screws 45 in top plate 40 permit rotational adjustment in smaller increments, such as 5°. Alternatively, coarse limit screw 55 and fine adjustment screw 45 may permit a range of motion of moveable plate 50 relative to fixed plate 30 in any increment between 0° and 360° and in increments as low as 2.5° and less. As shown in a specific embodiment of this invention in FIG. 1, coarse adjustment screws 55 are positioned within moveable plate 50 to permit virtually zero movement between moveable plate 50 and fixed plate 30.

Fine adjustment means 44 preferably comprise fine limit screws 45 which may be positioned within threaded bores 47 in fixed plate 30. As described above, fine limit screw 45 preferably obstructs a range of motion of coarse limit screw 55. Fine limit screws 45 are preferably connected with respect to threaded bore 47 in top plate 40 of fixed plate 30. As a result, coarse limit screws 45 are preferably positioned on each side of moveable plate 50 and fine limit screws 45 are positioned at either end of the range of motion of moveable plate 50, such as within fixed plate 30.

Alternatively, fine adjustment means may comprise a member that includes a length that may be inwardly or outwardly adjustable to create an obstruction for the coarse limit screws 55. Alternatively, fine adjustment means 44 may comprise an expandable or contractible member positioned in either fixed plate 30 or moveable plate 50. Ideally, fine adjustment means 44 would comprise a component or mechanism that is integrated with joint 20 and would not result in loose parts that may be discarded or misplaced.

Depending upon the desired degree of fine adjustment required, fine. limit screw 45 may have a head of a predetermined length, such as a head that limits the range of motion of moveable plate 50 by 5° or by 2.5°. According to one preferred embodiment of this invention, fine limit screws 45 are color-coded depending upon the length of the head, i.e. a red fine limit screw is equal to a 2.5° reduction and a blue fine limit screw is equal to a 5° reduction in range of motion. Fine adjustment screws 45 may include washers or vary in length to accommodate a range of adjustments. For example, one or more washers may be positioned with fine limit screws 45 to require only a single size of fine limit screw 45 with multiple configurations possible depending upon placement of washers under the head of fine limit screw 45. In addition, fine limit screws 45 may be removed altogether to permit a more coarse adjustment of joint 20.

Figures 7, 8, 9:
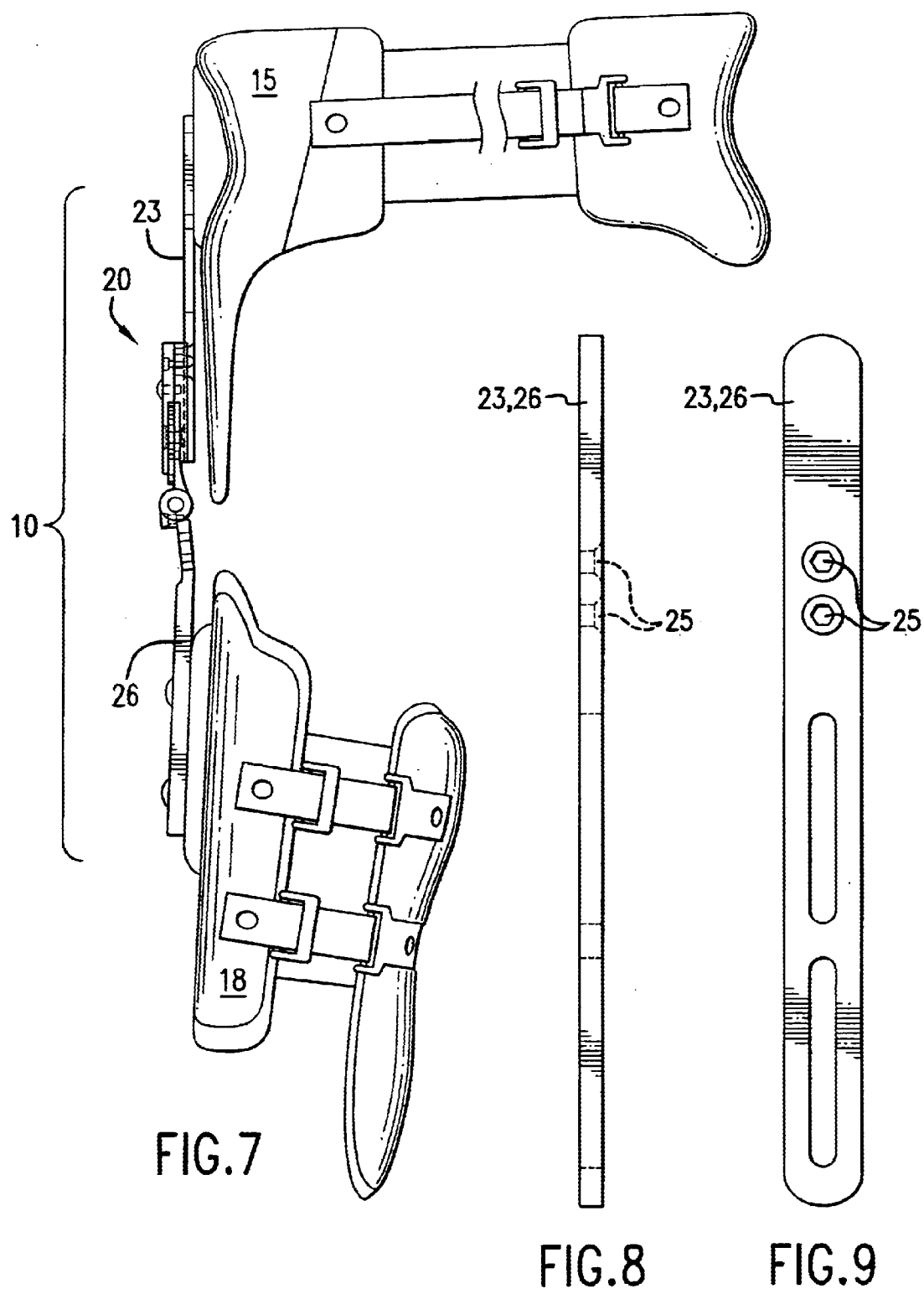
FIG. 7 is front view of a joint positioned in an orthopedic hip brace according to one preferred embodiment of this invention.
FIG. 8 is a side view of a strut according to one preferred embodiment of this invention.
FIG. 9 is a front view of the strut shown in FIG. 8.

Fixed plate 30 is preferably connected at one end with respect to first strut 23. First strut 23 is connected at an opposite end with respect to a portion of orthopedic brace 10, such as the hip brace as shown in FIG. 7. Moveable plate 50 is preferably connected with respect to second strut 26. Second strut 26 is connected at an opposite end with respect to an opposite portion of orthopedic brace 10, such as the thigh cuff as shown in FIG. 7. First strut 23 and second strut 26, as used herein, are defined by their location not by different physical characteristics. A representative first strut 23 and/or second strut 26 are shown in FIGS. 8 and 9. As a result of the described configuration, and as shown in FIG. 7, first strut 23 is pivotable with respect to second strut 26.

According to a preferred embodiment of this invention and in accordance with an object of this invention, first strut 23 and/or second strut 26 are interchangeable with at least one other strut, such as a third strut having a different size than either first strut 23 or second strut 26. Depending upon the application, the size of patient, the configuration of orthopedic brace, the maker of the equipment and other factors, different sized struts may be necessary. As such, universal mounting plate 35 is integrated with moveable plate 50. Universal mounting plate 35 is preferably attachable to at least two different sizes of struts and more preferably is attachable to most commercially available struts. Struts 23, 26 may further include mounting apertures 25 that facilitate connection to universal mounting plate 35 and thus joint 20.

According to one preferred embodiment of this invention, joint 20 further comprises hinge 70 connecting first strut 23 with respect to fixed plate 30, specifically either top plate 40 and bottom plate 60. Hinge 70 according to one preferred embodiment of this invention is best shown in FIGS. 1–3.

Figure 10:
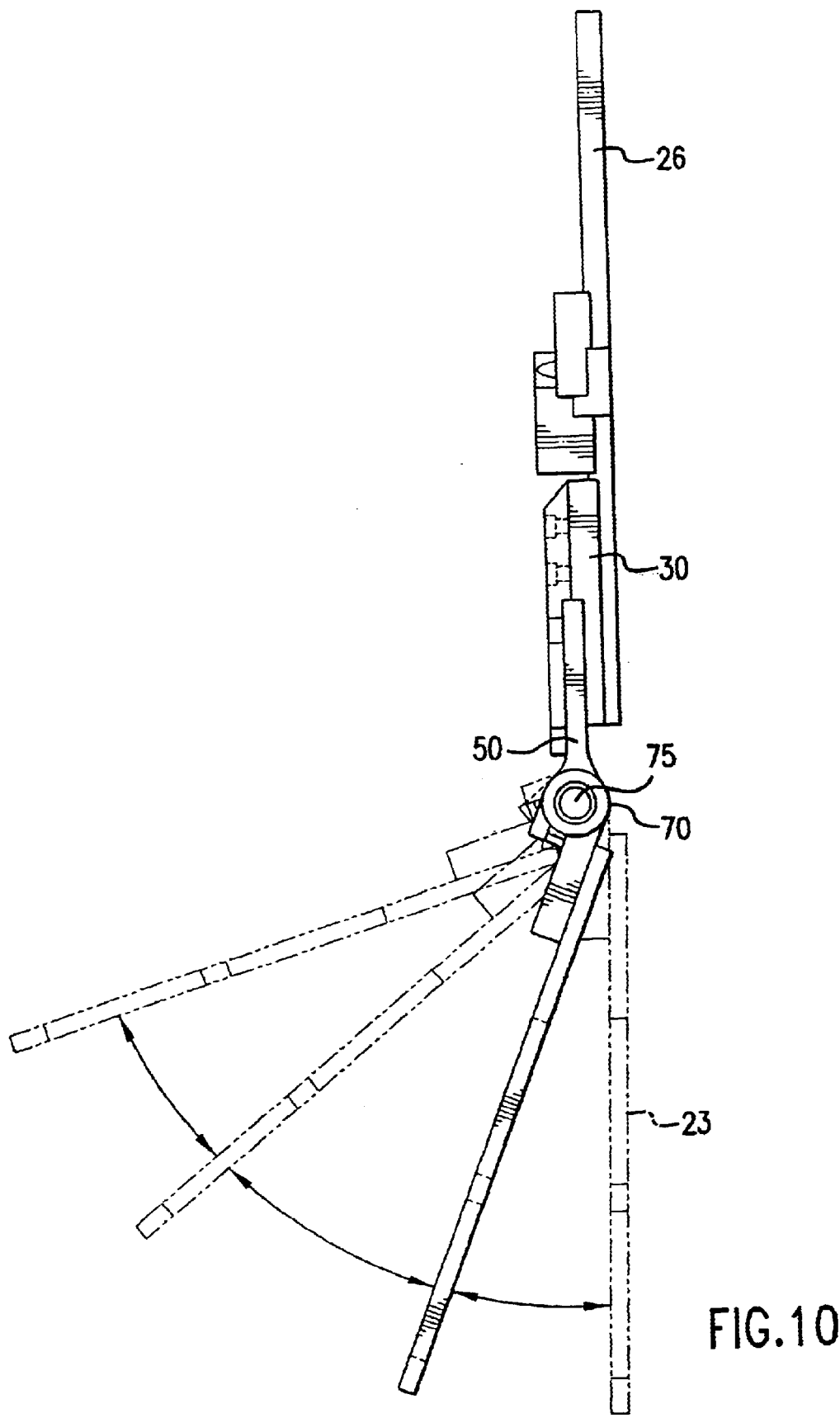
FIG. 10 is a side view of the joint showing movement of the hinge through various positions.

Hinge 70 preferably includes hinge pin 75 and set screw 77 which, in one preferred embodiment of this invention, tightens a collar of hinge 70 around hinge pin 75 and thus maintains a fixed position between first strut 23 and moveable plate 50. In one preferred embodiment of this invention, hinge pin 75 includes a knurled or otherwise textured outer surface to increase the gripping strength between hinge 70 and hinge pin 75. Depending upon the configuration of orthopedic brace 10 and the size of the patient, it may be necessary to adjust the position between first strut 23 and joint 20 around a second axis of rotation centered through an axis of hinge pin 75. FIG. 10 shows the movement of first strut 23 around the second axis of rotation, or in hip brace applications abduction and adduction adjustment. Clearly, the second axis of rotation between first strut 23 and joint 20 is different from the first axis of rotation between moveable plate 50 and fixed plate 30 of joint 20.

Figure 11:
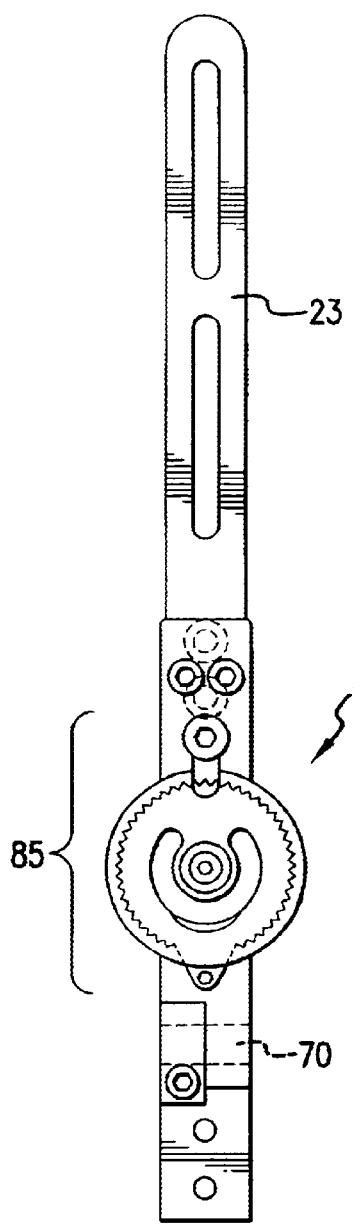
FIG. 11 is a front view of a joint according to another preferred embodiment of this invention.
Figure 12:
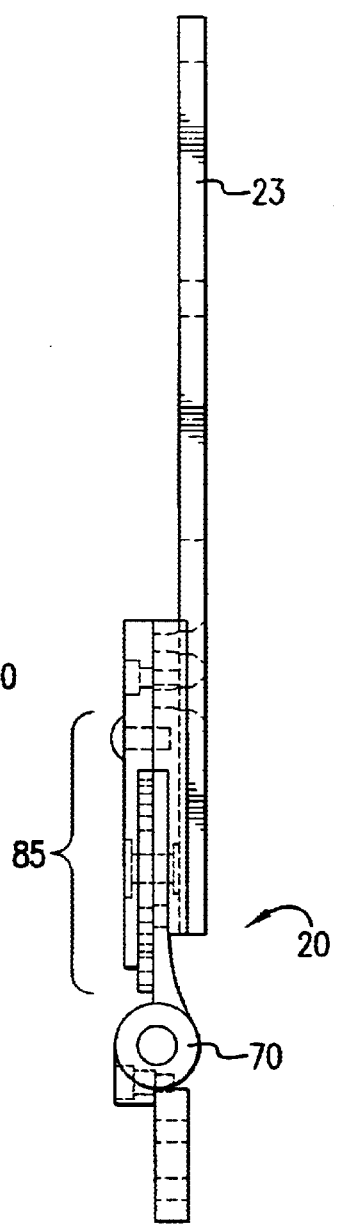
FIG. 12 is a side view of the joint shown in FIG. 11.
Figure 13:
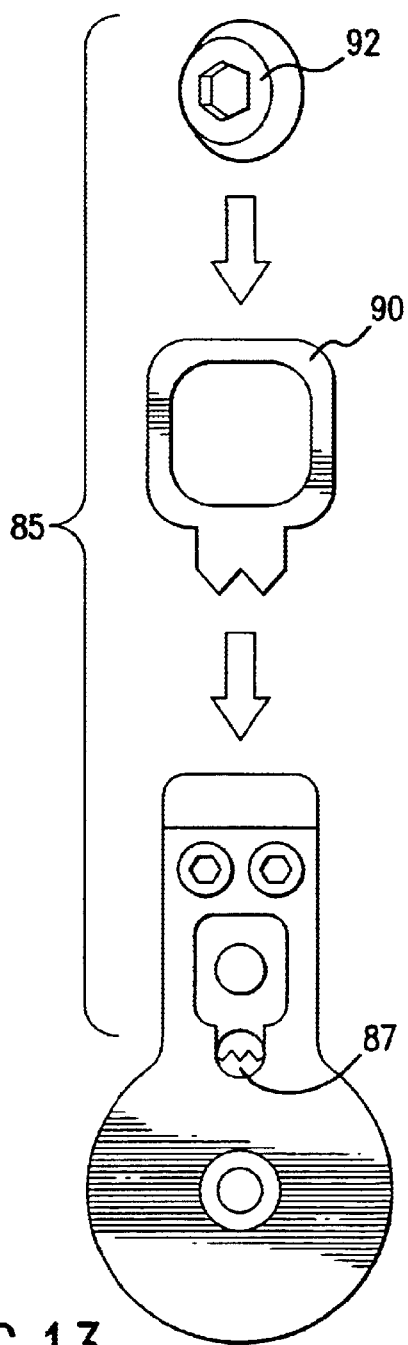
FIG. 13 is a front exploded view of the movement assembly for the joint shown in FIG. 11.

According to another preferred embodiment of this invention shown in FIGS. 11–13, joint 20 may alternatively comprise ratchet mechanism 85 that permits adjustment within an arc of rotation between fixed plate 30 and moveable plate 50. Ratchet mechanism 85 may include teeth 87 which are set into place with cam lock 90 and cam screw 92, as best shown in FIG. 12.

Figure 14:
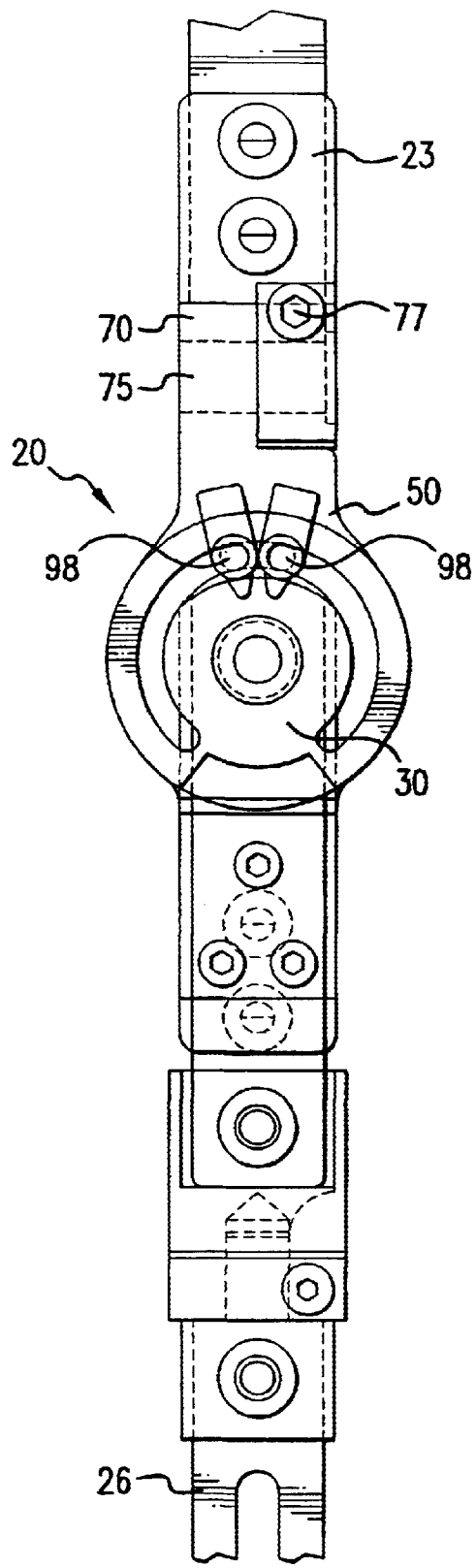
FIG. 14 is a front view of a joint according to yet another preferred embodiment of this invention.
Figure 15:
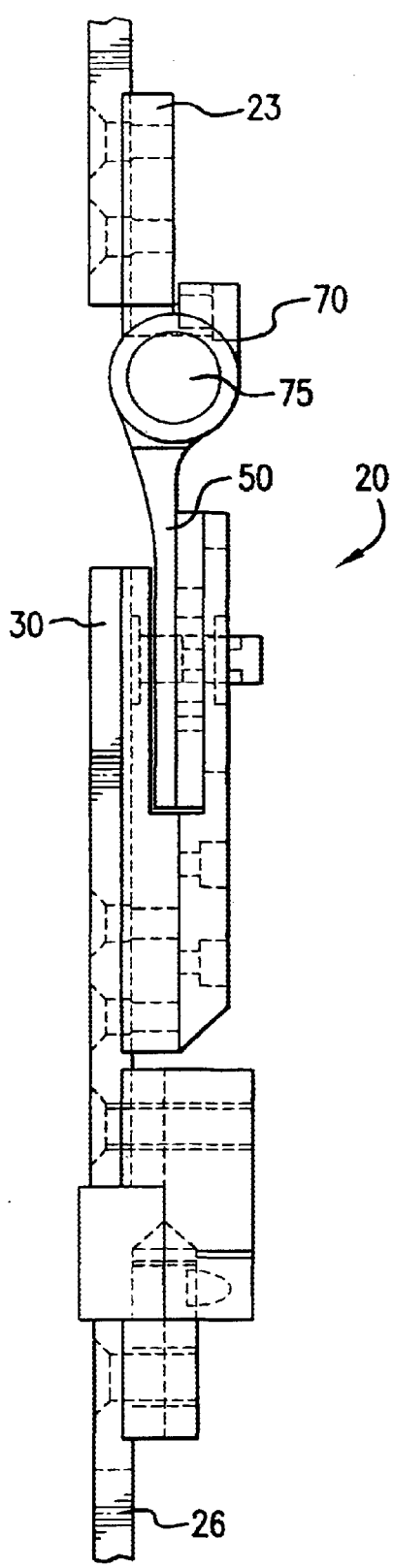
FIG. 15 is a side view of the joint shown in FIG. 14.

According to another preferred embodiment of this invention shown in FIGS. 14 and 15, joint 20 may alternatively comprise groove 95 within which one or more, and preferably two, c-clamp locks 98 are adjustably positioned to facilitate movement between two outer limits within the desired arc of rotation.

While in the foregoing specification this invention has been described in relation to certain preferred embodiments thereof, and many details have been set forth for purpose of illustration, it will be apparent to those skilled in the art that the. method and apparatus according to this invention are susceptible to additional. embodiments and that certain of the details described herein can be varied considerably without departing from the basic principles of the invention.

I claim:

1. An articulating joint for an orthopedic brace comprising:
   a bottom plate;
   a moveable plate rotatably connected with respect to the bottom plate, the moveable plate having a plurality of adjustment apertures positioned around an axis of rotation;
   a top plate positioned over the moveable plate and fixed with respect to the bottom plate;
   at least one coarse limit screw positioned within an adjustment aperture of the plurality of adjustment apertures; and
   at least one fine limit screw positioned with respect to one of the top plate and the bottom plate, the at least one coarse limit screw and the at least one fine limit screw interfering with each other to limit rotation of the moveable plate relative to the bottom plate between any two desirable angles of rotation greater than 0° and less than 360° around the axis of rotation.

2. An articulating joint for an orthopedic brace comprising:
   a fixed plate;
   a moveable plate rotatably connected with respect to the fixed plate, the moveable plate having a plurality of adjustment apertures positioned around a first axis of rotation;

a coarse limit screw positioned within an adjustment aperture of the plurality of adjustment apertures; and fine adjustment means positioned with respect to the fixed plate, the fine adjustment means obstructing a range of motion of the coarse limit screw, wherein the coarse adjustment screw and the fine adjustment means permit a range of motion of the moveable plate relative to the fixed plate between greater than 0° and less than 360° in increments of 2.5°.

3. An articulating joint for an orthopedic brace comprising:

a fixed plate;

a moveable plate rotatable connected with respect to the fixed plate, the moveable plate having a plurality of adjustment apertures positioned around a first axis of rotation;

a coarse limit screw positioned within an adjustment aperture of the plurality of adjustment apertures;

fine adjustment means positioned with respect to the fixed plate, the fine adjustment means obstructing a range of motion of the coarse limit screw;

a hinge attached to the moveable plate;

a first strut connected with respect to the hinge, the first strut rotatable with respect to the moveable plate around a second axis of rotation different from the first axis of rotation.

4. The articulating joint of claim 3 further comprising a knurled hinge pin positioned within the hinge.

5. The articulating joint of claim 3 further comprising a universal mounting plate connected with respect to the moveable plate, the universal mounting plate attachable to at least two different sizes of struts.

6. The articulating joint of claim 3 wherein the coarse adjustment screw and the fine adjustment means permit a range of motion of the moveable plate relative to the fixed plate between greater than 0° and less than 360° in increments of 2.5°.

7. The articulating joint of claim 3 wherein the fixed plate comprises a top plate and bottom plate positioned around the moveable plate.

8. An articulating joint for an orthopedic brace comprising:

a fixed plate;

a moveable plate rotatably connected with respect to the fixed plate;

a coarse limit screw positioned within the moveable plate; and fine adjustment means positioned within the fixed plate, the fine adjustment means obstructing a range of motion of the coarse limit screw between any two desirable angles of rotation greater than 0° and less than 360° around an axis of rotation.

9. The articulating joint of claim 8 wherein a coarse limit screw is positioned on each side of the moveable plate and a fine limit screw is positioned at either end of the range of motion of the moveable plate.

10. The articulating joint of claim 8 further comprising a universal mounting plate connected with respect to each of the moveable plate and the fixed plate, the universal mounting plate connectable to at least two sizes of struts.

11. The articulating joint of claim 8 further comprising a hinge connecting the moveable plate to a first strut, the hinge having a knurled hinge pin therethrough.

12. The articulating joint of claim 8 further comprising an axis pin connecting the moveable plate with respect to the fixed plate, the axis pin following an axis of rotation of the moveable plate.

13. An articulating joint for an orthopedic brace comprising:

a bottom plate;

a moveable plate rotatably connected with respect to the bottom plate, the moveable plate having a plurality of adjustment apertures positioned around an axis of rotation;

a top plate positioned over the moveable plate and fixed with respect to the bottom plate;

at least one coarse limit screw positioned within an adjustment aperture of the plurality of adjustment apertures;

at least one fine limit screw positioned with respect to one of the top plate and the bottom plate;

a hinge attached to the moveable plate; and a first strut connected with respect to the hinge, the first strut rotatable with respect to the moveable plate around a second axis of rotation different from the first axis of rotation.

14. The articulating joint of claim 13 further comprising a first strut connected with respect to one of the top plate and the bottom plate and a second strut connected with respect to the moveable plate, the first strut pivotable with respect to the second strut.

15. The articulating joint of claim 14 further comprising a hinge connecting the first strut with respect to one of the top plate and the bottom plate.

16. The articulating joint of claim 15 further comprising a hinge pin positioned within the hinge, the hinge pin having a knurled outer surface.

17. The articulating joint of claim 14 wherein the first strut is interchangeable with a third strut having a different size than the first strut.

18. The articulating joint of claim 14 wherein the second strut is interchangeable with a third strut having a different size than the second strut.

19. The articulating joint of claim 13 wherein the plurality of adjustment apertures each comprise a threaded bore.

20. The articulating joint of claim 13 wherein the at least one fine limit screw is connected with respect to a threaded bore in the top plate.

21. The articulating joint of claim 13 wherein the at least one fine limit screw has a head of a predetermined length and is color-coded depending upon the length of the head.

* * * * *